United States Patent [19]
Sörnmo et al.

[11] Patent Number: 5,690,118
[45] Date of Patent: Nov. 25, 1997

[54] METHOD AND APPARATUS FOR CORRECTING NON-PHYSIOLOGICAL VARIATIONS IN ECG SIGNALS

[75] Inventors: Leif Sörnmo, Lund; Peter Karlsson; Lena Lundström, both of Stockholm, all of Sweden

[73] Assignee: Siemens Elema AB, Solna, Sweden

[21] Appl. No.: 704,108

[22] Filed: Aug. 28, 1996

[30] Foreign Application Priority Data

Sep. 1, 1995 [SE] Sweden ................................ 9503019

[51] Int. Cl.$^6$ ........................................... A61B 5/0402
[52] U.S. Cl. ............................................. 128/696
[58] Field of Search ........................ 128/696, 699, 128/901; 364/413.06

[56] References Cited

U.S. PATENT DOCUMENTS

| | | | |
|---|---|---|---|
| 5,092,341 | 3/1992 | Keler | 364/413.06 |
| 5,188,116 | 2/1993 | Pommrehn et al. | |
| 5,348,020 | 9/1994 | Hutson | |
| 5,381,803 | 1/1995 | Herleikson et al. | |
| 5,421,342 | 6/1995 | Mortara | 128/696 |
| 5,433,208 | 7/1995 | Lundstrom et al. | |
| 5,469,856 | 11/1995 | Lundstrom et al. | |

FOREIGN PATENT DOCUMENTS

| | | |
|---|---|---|
| 0 255 348 | 3/1988 | European Pat. Off. |
| WO 94/26163 | 5/1994 | WIPO |

OTHER PUBLICATIONS

Kung et al, "A Frobenius Approximation Reduction Method (FARM) for Determining Optimal Number of Hidden Units," International Joint Conference On Neural Networks, Seattle, Washington, Jul. 8–14, 1991, pp. II–163—II–168.

Kyrkos et al, "QRS Detection Through Time Recursive Prediction Techniques," Signal Processing, vol. 15, No. 4, Dec. 1988, pp. 429–436.

Pahlm et al, "Data Processing of Exercise ECGs," IEEE Transactions on Biomedical Engineering, vol. BME–34, pp. 158–165, Feb. 1987.

Cruts et al, "Arrhythmia typification in a Real–Time Analysis System for Monitoring Geriatric Patients during Exercises," IEEE Proceedings from the Conference on Computers in Cardiology 1985, pp 423–426.

Alsté et al, "Beat–to–Beat Analysis of Waveshape and Rhythm in XECG Using Inner Vector Product Hardware," IEEE Proceedings from the Conference on Computers in Cardiology 1982, pp. 355–358.

(List continued on next page.)

Primary Examiner—William E. Kamm
Assistant Examiner—George R. Evanisko
Attorney, Agent, or Firm—Hill, Steadman & Simpson

[57] ABSTRACT

In a method for correcting for non-physiological variations in ECG signals, signals recorded during a heartbeat, or a characteristic part of a heartbeat, are conditioned and digitized. Signal samples are stored in the form of an m×p matrix, where m is the number of samples and p is the number of leads used from measuring electrodes applied to the patient. The difference between this measuring matrix and a reference matrix is minimized by performing one or more of the operations translation, time synchronization, rotation and scaling of the measuring matrix. An apparatus for correcting for non-physiological variations in ECG signals includes a stage for conditioning signals, picked up by measuring electrodes applied to the patient, an A/D converter for digitizing the signals and a calculation unit. The calculation unit includes a storage unit for storing signal samples in the form of a m×p matrix, where m is the number of samples and p is the number of leads used from measuring electrodes applied to the patient, and for storing a reference matrix. The calculation unit is arranged to minimize the difference between the measuring matrix, formed from signal samples, and the reference matrix by one or more of the operations of translation, time synchronization, rotation and scaling of the measuring matrix.

23 Claims, 4 Drawing Sheets

OTHER PUBLICATIONS

Rubel et al, "Methodology of ECG Interpretation in the Lyon Program", Meth. Inform. Med., vol. 29, No. 4, pp. 393–402, 1990.

Fayn et al, "Quantitative Assessment of Beat–to–Beat Variability in Ambulatory ECGT Recordings".

Rubel et al., "New Strategies in Serial ECG Comparison and Trend Analysis", Computer ECG Analysis: Towards Standardization, Elsevier Science Publishers B.V. (North–Holland), pp. 323–328, 1986.

Ben–Haim et al, "Beat–to–Beat Morphologic Variability of the Electrocardiogram for the Evaluation of Chest Pain in the Emergency Room," Am. J. Cardiol. 70, pp. 1139–1142. 1992.

Shaw et al, "On the Detection of QRS Variations in the ECG", IEEE Transactions on Biomedical Engineering, vol. 42, No. 7, pp. 736–741, Jul. 1995.

Sörnmo, "A Model–Based Approach to QRS Delineation", Computers and Biomedical Research, vol. 20, pp. 526–542, 1987.

Golub et al, "Matrix Computations", The Johns Hopkins University Press, 1989, Chapter 12.4, pp. 581–587.

Sörnmo, "Time–Varying digital filtering of ECG Baseline Wander", Medical & Biological Engineering & Computing, vol. 31, pp. 503–508, 1993.

METHOD AND APPARATUS FOR CORRECTING NON-PHYSIOLOGICAL VARIATIONS IN ECG SIGNALS

BACKGROUND OF THE INVENTION

1. Field of the Invention

The present invention relates to a method for correcting for non-physiological variations in ECG signals, the signals being recorded during a heartbeat or a characteristic part of a heartbeat and being conditioned and digitized, and to an apparatus for performing such a correction, including means for conditioning signals, picked up by measuring electrodes applied to the patient, an A/D converter for digitizing the signals and a calculation unit.

2. Description of the Prior Art

Variations in ECG signals from heartbeat to heartbeat, caused by the patient's breathing movements and possible changes in position, are a complication in a number of analysis made on ECG signals. Changes of this kind are mainly due to changes in the geometry of the torso and changes in the heart's relative position, i.e., changes in the heart's electrical axis in relation to the positions of the measuring electrodes employed. In e.g., morphology classification of QRS complexes, these variations in the ECG signal can cause QRS complexes representing identical heartbeats to be classified as different complexes due to changes in the ECG signals caused solely by geometric changes in the patient's torso. The problem is very significant in long-term patient monitoring. In these patients in particular, new "normal" QRS complexes occurring when the patient changes position are a risk. Moreover, serial comparison of a plurality of resting ECG's from the same patient often displays undesirable variability, because the placement of electrodes in relation to the heart is not identical in each examination. In variance ECG's in which beat-to-beat variability in the ECG signal is studied, these non-physiological variations in the ECG signals constitute a major complication, since these variations, occasioned e.g., by the patient's breathing, are often greater than the variability which is to be studied and which is related to the function of the myocardium.

A number of attempts have been made to remedy these problems, but the attempts have been inadequate or ineffective.

In the morphology classification of QRS complexes, attempts have been made e.g. to solve the problem indirectly by the use of extracted quantities, which to some extent are independent of the exact morphology of the complex, as a measure of the similarity of QRS complexes. Examples of such quantities are the width and area of a two-dimensional single-plane representation of the QRS complex. This type of morphology classification, however, generally yields poorer results than morphology classification based on the correlation between samples in the complexes, see Pahlm and Sörnmo, "Data Processing of Exercise ECGS", IEEE Transactions on Biomedical Engineering, vol. BME-34, pp. 158–165, February 1987, Cruts et al., "Arrhvthmia Typification in a Real-Time Analysis System for Monitoring Geriatric Patients during Exercises", Proceedings from the Conference on Computers in Cardiology IEEE 1985, pp. 423–426, and Alsté et al., "Beat-to-Beat Analysis of Waveshape and Rhythm in XECG Using Inner Vector Product Hardware", Computers in Cardiology, pp. 355–358, IEEE 1982.

The latter technique, however, based on correlation between samples in the complexes, is sensitive to respiratory variations, among others in the QRS complexes. Attempts to compensate for this usually employ updating of the reference complex or template by averaging, however, this method also has major limitations. Thus no technique is currently available for compensating for variations in the direction of the QRS complex's electric axis before the correlation to reference complexes is performed.

In serial comparisons of a number of resting ECGs recorded from the same patient on different occasions, there is often an undesirable variability because the location of electrodes in relation to the heart is not identical from one examination to another. One method for reducing this undesirable variability is described in Rubel et al., "Methodology of ECG Interpretation in the Lyon Program". Meth. Inform. Med. Vol. 29, no. 4, pp. 393–402, (1990), Fayn et al., "Quantitative Assessment of Beat-to-Beat Variability in Ambulatory ECG Recordings", and Rubel et al., "New Strategies in Serial ECG Comparison and Trend Analysis", Computer ECG Analysis: Towards Standardization, Elsevier Science Publishers B.V. (North-Holland), pp. 323–328 (1986), in which method geometric transformations of three-dimensional vector loops are performed. Thus, this method requires recording of a so-called vector cardiogram, which means that the electrodes are positioned so three orthogonal leads are obtained. The method is relatively complex and in addition thereto an iterative process which is hard to implement in real time, i.e. hard to apply to beat-to-beat variability.

Variance ECG, i.e. beat-to-beat variability in the ECG signal, is studied in order to diagnose ischemic heart disease, cf. Prasad and Gupta, "Phase-Invariant Signature Algorithm". "A noninvasive Technique for Early Detection and Quantification of Quabain-induced Cardiac Disorders"; Angiology 30, pp. 721–732 (1979), and Ben-Haim et al., "Beat to Beat Variation in Healed Myocardial Infarction". Am J Cardiol 1992, 70: pp. 1139–1142. In U.S. Pat. No. 5,188,116, one such technique for detecting ischemic heart disease with the aid of variance ECG is described in which correction of respiratory variability in the ECG signal is performed by a scaling of QRS complexes based on the amplitude of the R-spike, see also Shaw and Savard, "On the Detection of QRS Variations in the ECG", IEEE Transactions on Biomedical Engineering, Vol. 42, No. 7, pp. 736–741, (July 1995).

SUMMARY OF THE INVENTION

An object of the present invention is to overcome the above-discussed disadvantages of the known techniques in a method and an apparatus for correcting for non-physiological variations in ECG signals. In this application, the term "non-physiological" refers to variations which are not caused by the heart's electrical activity.

The above object is achieved in accordance with the principles of the present invention in a method and apparatus for correcting for non-physiological variations in ECG signals which are recorded during a heartbeat, or a characteristic portion of a heartbeat, wherein the signals are conditioned and digitized to produce signal samples, the signal samples are stored in the form of an m×p measuring matrix wherein m is the number of samples and p is the number of leads (measuring electrodes) used to obtain the signals, and wherein a difference between this measuring matrix and a reference matrix is minimized by one or more of the matrix operations of translation, time synchronization, rotation and scaling, operated on the measuring matrix.

The invention can be implemented and utilized in an ECG apparatus which perform various kinds of analysis of ECG signals. The invention is especially useful for analysis based on the comparison of signals from the same patient on different occasions. An example of such an analysis is the morphology classification of QRS complexes which form the basis of substantially all other ECG analysis in both diagnosis and monitoring. Other examples of applications for the invention are serial comparison of stored resting ECGs from the same patient and variance ECGS, whereby effective correction is provided of non-physiological beat-to-beat and day-to-day ECG signal variability, mainly caused by changes in the heart's position in relation to the electrodes because of e.g., breathing movements or differences in electrode placement.

In each of the method and apparatus according to the invention, signals from measuring electrodes applied to a patient are thus sampled and stored. The signal is recorded during a heartbeat or a characteristic part of a heartbeat, such as the QRS complex. Methods for determining the beginning and the end of QRS complexes are known, cf. e.g., Sörnmo, "A Model-Based Approach to QRS Delineation", Computers and Biomedical Research, vol. 20, pp. 526–542 (1987). The recorded signal is stored in an m×p matrix where m is the number of samples, i.e., represents the length of the complex, since a complex is normally measured in the number of samples, and the distance between each sample is appropriately constant, and p is the number of leads which are used from the applied electrodes.

The difference between two such matrices, derived from different occasions, is then minimized by the performance of operations which only correct geometric, non-physiological variability in the above expression's previously specified meaning. The operations used are translation, time synchronization, rotation and scaling.

If two such matrices are designated A and B respectively, where A is the reference matrix, the translation can be performed by subtracting constant values, i.e., DC levels, from each line in matrix B. However, a better method is to perform baseline filtration of the signal, with the aid of a more advanced algorithm, before it is stored in the matrix. According to an embodiment of the apparatus of the invention, the conditioning means include a high-pass filter, arranged to filter out baseline variations from the ECG signals. In other words, translation is performed before the difference between matrices A and B is minimized.

According to an embodiment of the method of the invention, measurement data stored in the measuring matrix are shifted, for the time synchronization, one sample for every new measuring matrix, whereupon the measuring matrix exhibiting the smallest difference compared to the references matrix is selected as the time-synchronized measuring matrix. Minimization is consequently performed for a number of B matrices. If it is assumed that the QRS detection point supplies a rough estimate of the synchronization point, minimization can be performed for e.g., ten B matrices, which thus contain 5 samples shifted in either direction in relation to the synchronization point.

Rotation is performed by multiplying the matrix B by a matrix Q which only performs a rotation of the matrix B without changing the lengths of the vectors or the inter-vector angle. Such a matrix is said to be orthogonal and is characterized by the fact that a unitary matrix is obtained, in which all the elements are zero except for diagonal elements which are equal to 1, when the matrix is multiplied by its transpose, i.e., reflection in the diagonal.

Scaling is performed by multiplying the matrix by a scale factor.

According to another embodiment of the invention the Frobenius norm, obtained by subtracting one matrix from the other, is determined as a measure of the difference between the matrices. The Frobenius norm is calculated by adding the squared sum of all the elements in the matrix and determining the square root of this sum.

The problem of minimizing the difference between the A and B matrices can be mathematically expressed as follows:

Minimize $\|A-\alpha B(\tau)Q\|_F$ under the condition $Q^T Q = I_p$ in which $\alpha$=the scale factor Q=the rotation matrix (p×p)

$\tau$=the time shift (e.g. [−5..5])

$\| \|_F$ designates the Frobenius norm.

$$\|A\|_F = \sqrt{\sum_{i=1}^{m} \sum_{j=1}^{n} |a_{ij}|^2}$$

where A=an m×n matrix and $a_{ij}$ designates sampled signal values.

Time shift minimization, for the time synchronization, is performed by calculating optimum scaling and rotation for a number of matrices and then selecting the matrix yielding the smallest value for the difference.

The solution of problems of the kind formed by minimization of the difference between matrices with respect to scaling and rotation is partially well-known, cf e.g. Golub and Van Loan, Matrix Computations, The Johns Hopkins University Press (1989), chap. 12.4, pp. 581–587. It appears that exact expressions for the rotation matrix Q and the scaling factor $\alpha$ can be formulated. In calculation of the rotation matrix Q, singular value factorization is employed, which means that the matrix is re-written as the product of two orthogonal matrices and a diagonal matrix. The rotation matrix Q, yielding optimum rotation, is given by the product of the two orthogonal matrices, obtained in singular value factorization of the transponate of matrix B, multiplied by matrix A.

The optimum scaling factor $\alpha$ is obtained by forming the sum of the diagonal elements in the quadratic matrix, obtained by multiplying the transponate of the optimally rotated B matrix by matrix A and dividing with the sum of the diagonal elements in the matrix obtained, when matrix B is multiplied by its own transponate.

The matrix Q and the factor $\alpha$ can then be mathematically derived in the following manner.

The minimum of the expression $$\|A-\alpha BQ\|_F^2 = sp(A^T A) + \alpha^2 sp(B^T B) - 2\alpha sp(Q^T B^T A),$$

where sp(X)=the sum of the diagonal elements in a quadratic matrix X, is obtained, for a fixed $\alpha$, by maximizing $Sp(Q^T B^T A)$.

The Q which maximizes this expression is equal to $UV^T$, where the matrices U and V are obtained by calculating singular value factorization, SVD, from $B^T A$, see Golub and Van Loan, chap. 12.4.1 for derivation.

Minimization with respect to $\alpha$ is performed by setting the corresponding derivative equal to zero, i.e.

$$2\alpha sp(B^T B) - 2sp(Q^T B^T A) = 0$$

which yields $$\alpha = sp((BQ)^T A)/sp(Q^T B^T A) = 0$$

which yields $$\alpha = sp((BQ)^T A)/sp(B^T B).$$

Thus, the principle of the invention is to use the above-described method for transforming stored heartbeats, or characteristic parts thereof, such as QRS complexes, so non-physiological variability, in the sense specified above, is minimized in an optimal manner in relation to a reference complex before the complexes are subjected to further analysis.

According to another embodiment of the method of the invention, the rotation and scaling operations are performed simultaneously.

In another embodiment of the method of the invention, a predefined number of selected measuring matrices are corrected, for determination of a reference matrix, according to one or more of the above operations, using one of the measuring matrices as a temporary reference, whereupon the average value of the corrected matrices is formed and this average value is set as the reference matrix. After a quality check, a first QRS complex, for example, is thus set as a temporary reference. A number of subsequent complexes are then rotated and scaled, and an average value is formed. The procedure can be repeated with the next consecutive measuring matrix, the immediately preceding average value serving as a reference value, until the resultant change in the average value and, accordingly, in the reference matrix drops below predefined limits. Measuring matrices which, after correction, deviate too much from the existing reference matrix, as measured by the Frobenius norm, are excluded from the mean value calculation, according to another method according to the invention.

In the correction of ECG signals according to the invention ensuring that medical information is not distorted is of the utmost importance.

It would also be advantageous to utilize the invention for correcting signals recorded in so-called patient monitoring, when the patient e.g. turns over at times causing geometric changes of the torso.

The ORS complex has been described above as a characteristic part of a heartbeat, but the invention is also applicable to other parts of a heartbeat, e.g., the P wave.

DESCRIPTION OF THE DRAWINGS

One exemplary embodiment of the apparatus according to the invention, applied to morphology classification of ECG in an analysis ECG recorder, will now be described in greater detail, referring to attached drawings.

DESCRIPTION OF THE PREFERRED EMBODIMENTS

Figure 1:
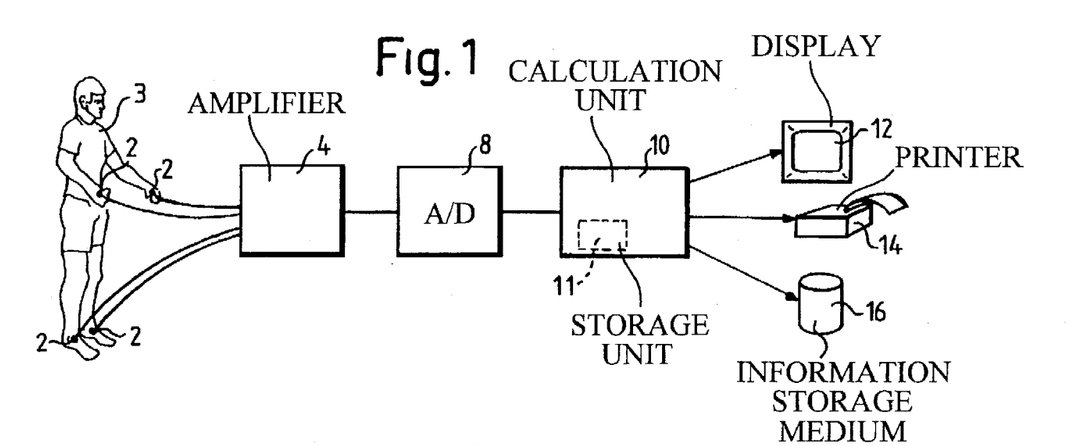
FIG. 1 is a block diagram showing an apparatus for recording and analyzing ECGs.

FIG. 1 shows an apparatus for recording and analyzing ECG signals measured with electrodes 2 applied to a patient 3. The signals from the electrodes 2 are supplied to an amplifier 4, any analog filters which may be used and an A/D converter 8. A calculation unit 10 includes a storage unit 11 for storing signal samples in the form of an m×p matrix, where m is the number of samples and p is the number of leads from measuring electrodes 2 applied to the patient 3, and for storing a reference matrix, is connected to the output of the analog filter stage (if used) and the A/D converter 8. The calculation unit 10 performs analysis of sampled ECG signals, and the results are presented on a display 12 or printer 14 or are stored on an information storage medium 16, such as a hard disk.

The apparatus according to the invention is housed inside the calculation unit 10 which comprises one or more microprocessors.

Figure 2:
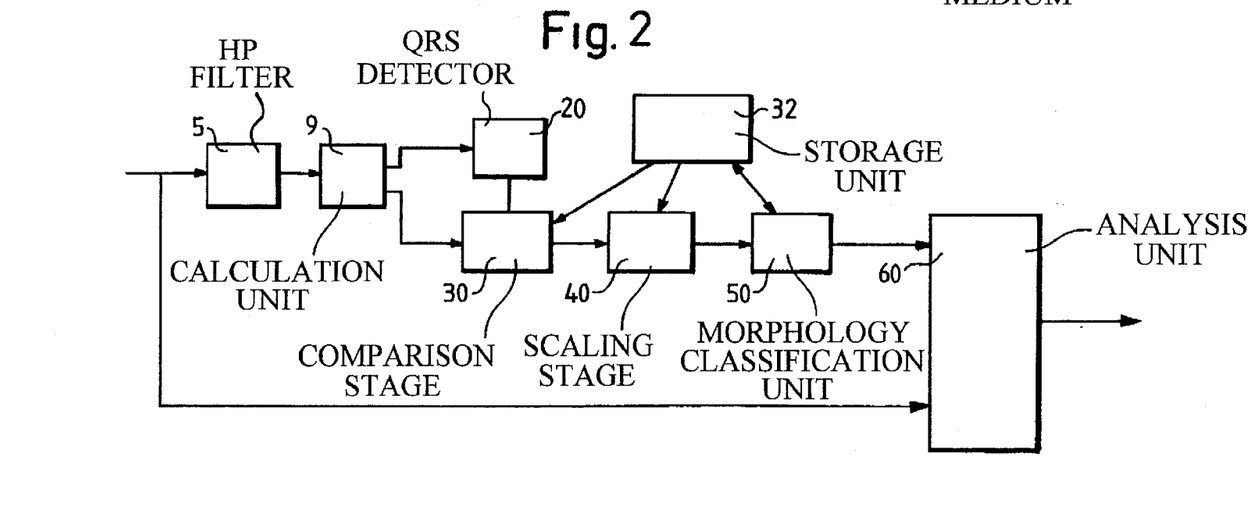
FIG. 2 is a schematic flow diagram illustrating the operation of the apparatus in FIG. 1.
Figure 3A:
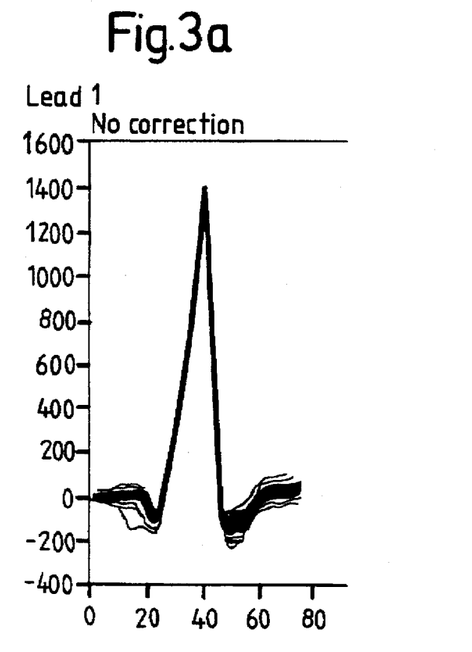
FIGS. 3a and 3b, 4a and 4b, and 5a and 5b show the QRS complex from 50–60 heartbeats from a 3-lead ECG recording, plotted in the same diagram after time synchronization, without correction and with correcting optimum rotation and scaling according to the invention, the first heartbeat being used as a reference.
Figure 3B:
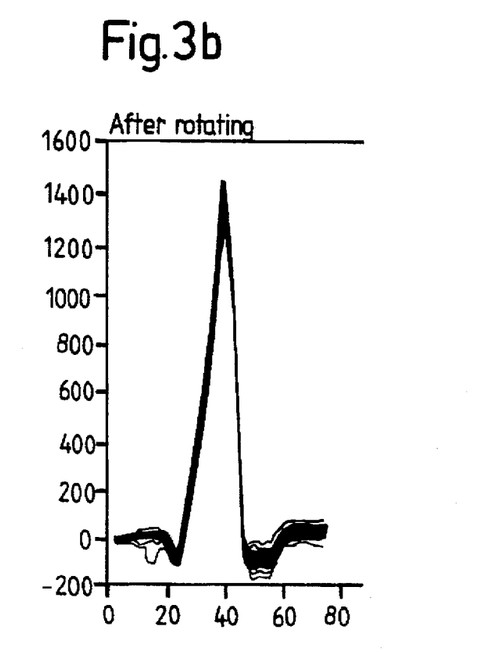
Figure 4A:
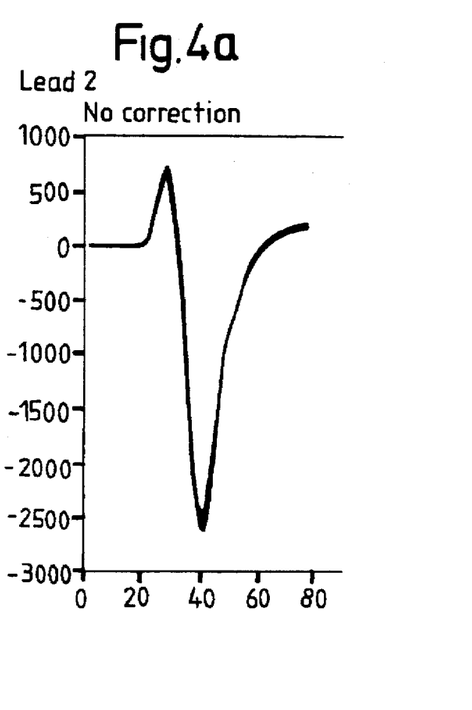
Figure 4B:
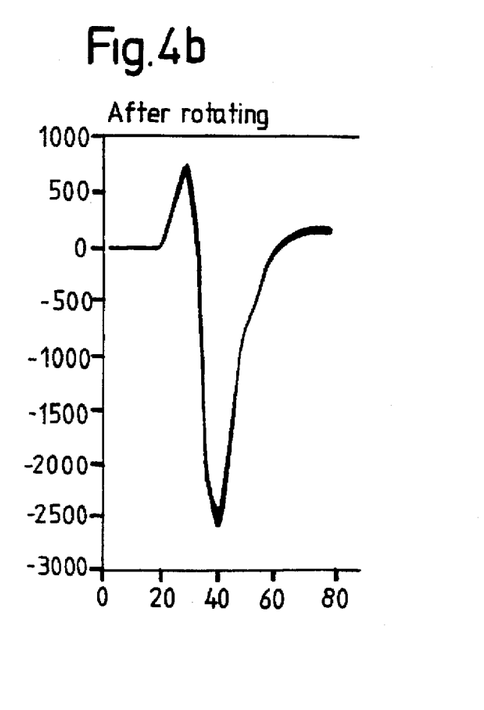
Figure 5A:
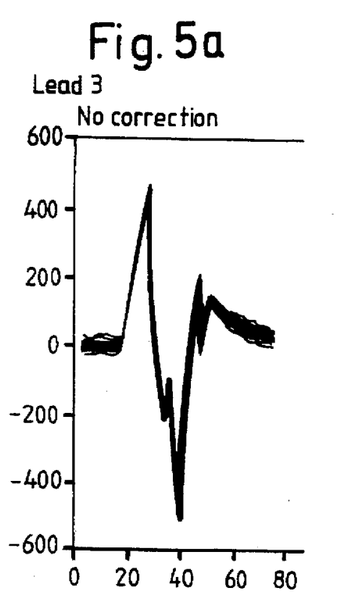
Figure 5B:
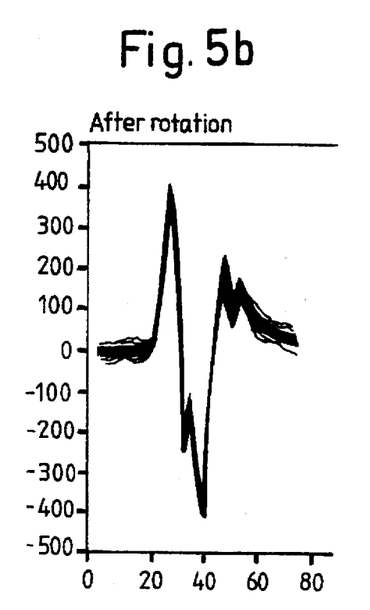

In the present embodiment, the analysis of ECG signals is adapted for morphology classification of cardiac cycle waveforms and is described below in greater detail, referring to FIG. 2.

The sampled leads are filtered with a suitable digital high pass filter 5, arranged in the unit 10 in FIG. 1, in order to eliminate baseline variations. Examples of suitable high pass filters are described in the publications WO 92/15242 and WO 92/15243 and in Sörnmo, "Time-Varying Digital Filtering of ECG Baseline Wander", Medical & Biological Engineering & Computing, Vol. 31, pp. 503–508, (1993).

A selection and calculation unit 9 selects and calculates, 10 from the filtered leads, the leads to be used for the detection and classification of the QRS complexes, preferably three orthogonal leads are used.

High pass filtering can possibly be performed after the selection or calculation operation.

The apparatus further has a ORS˙ detector 20, and each detected QRS complex is compared with references, based on previously recorded QRS complexes, in a time synchronization and comparison stage 30, and the detected QRS complex is compared to a reference point in the reference complexes.

The QRS detector 20 is of an appropriate, previously known type. The comparison and time synchronization can be based on calculations of cross-correlation between the current ORS complex and the reference complex according to the method described in greater detail below.

A detected QRS complex is rotated and scaled in the rotation and scaling stage 40 in a way described in greater detail below, and this is followed by morphology classification in a morphology classification unit 50. The morphology classification can then be performed with much greater reliability than has previously been possible. The classification of the QRS complex is then used for further analysis in an analysis unit 60. Examples of such analysis, based on morphology classification and which can be performed in the analysis unit 60, are averaging for S-T measurements and heart rhythm analysis.

If it is assumed that up to five references, representing five different kinds of heartbeats (cardiac cycles), i.e. five different QRS complex morphologies, are stored in the storage unit 32, new QRS complexes are appropriately created each time a new, measured QRS complex is not sufficiently similar to existing references, i.e. the correlation or the Frobenius norm, calculated according to the following with existing references, is below a predefined threshold value.

An efficient procedure for creating references is a basic prerequisite for reliable morphology classification.

The simplest way to achieve this is to use the first occurring QRS complex of each type as a reference. The obvious shortcoming of this method is the risk of getting references very much disturbed by noise. A common solution to this problem is to form an average value of a number of QRS complexes in order to reduce the noise level. Such a procedure is not suitable for use in the present invention, however, because an average value for any variations in the position of the electrical axis would also be formed instead of "capturing" a directions.

One procedure for achieving noise-free, representative references is instead based on an iterative use of the invention. In one such method, optimum rotation and scaling according to the invention are performed on a number, e.g. 20, of QRS complexes of the same type, with one of them serving as a temporary reference, during a "learning phase", and then forming the average value for beats corrected in this manner. The procedure can then be repeated an optional number of times with the mean value as a reference until no additional improvement is obtained for the reference. The procedure can be additionally refined by excluding QRS complexes which deviate too much from the existing reference, measured with the Frobenius norm below, after optimum rotation and scaling, before the average value is formed.

Signal samples in the form of an m×p matrix, where m is the number of samples and p is the number of leads used from measuring electrodes applied to the patient, are stored in the storage unit 32. Sample values thus form the matrix points. The length of the QRS complex is appropriately measured in the number of samples m, the distance between each sample being constant. The number of samples m can either be a fixed number of samples or can be selected from calculation of the start and end points of the QRS complex.

In the following description Ti designates the m×p matrix representing the reference complex number i(i=1–5 according to the above), and $B_i$ designates the m×p matrix containing the most recently detected QRS complex after time synchronization to reference complex number i in the comparison and time synchronization stage 30. Subsequent calculations to correct the direction of the electrical axis of each QRS complex, represented by the matrix Bi in relation to the reference matrix Ti, are performed in the rotation and scaling stage 40.

1. $C=B_i^T T_i$ is calculated
2. Singular value factorization of C is calculated: $U^T C V = \Sigma$
3. $Q=UV^T$ is calculated
4. $B'_i = B_i Q$
5. $\alpha = SP(B'^T_i T_i)/sp(B'^T_i B_i)$ is calculated
6. $B_i$ is replaced with $B_i^{opt} = \alpha B'_i$ If e.g., the cross-correlation between the measured QRS complex and stored references is used for the time synchronization in the comparison and time synchronization stage 30, it is possible to elect to correct only those QRS complexes for which the corresponding matrix Bi exhibits sufficiently high correlation with the corresponding reference matrix $T_i$. This will save processing capacity by, at an early stage, excluding morphological classes whose reference complexes are completely different from the current complex.

Time synchronization in the comparison and time synchronization stage 30 can be performed on the basis of the cross-correlation between the current QRS complex and the reference complex. The above procedure can also be implemented in the stage 30 for time synchronization of the current QRS complex with the reference complex. The stage 30 and the stage 40 can then be incorporated into a single unit in which the steps 1 to 6 above are performed a number of times with ECG data in the matrix B shifted one sample between each calculation. The optimum time synchronization (also rotation and scaling) is then given by the difference matrix with the smallest Frobenius norm.

The optimum time-synchronized, scaled and rotated matrix $B_i$ is then used as input data for the morphology classification unit 50 in which the classification category is determined for the current QRS complex. Several methods for morphology classification are known, usually based on calculation of the cross-correlation between the current QRS complex and a reference complex. The correlation coefficient p is then calculated for each lead.

$$\rho = \frac{\sum_{i=\text{onset}}^{\text{offset}} (x_i - \bar{x})(y_i - \bar{y})}{\sqrt{\sum_i (x_i - \bar{x})^2 \sum_i (y_i - \bar{y})^2}}$$

where $$\bar{x} = \frac{1}{\text{offset} - \text{onset} + 1} \sum_{i=\text{onset}}^{\text{offset}} x_i$$

$$-1 \leq \rho \leq 1$$

where x=the heartbeat to be classified (one lead)
y=the reference.

The cross-correlation is suitably calculated between the starting point and the end point of the QRS complex, so the classification unit 50 suitably includes some technique for determining these points of QRS complexes in the morphology classification, see e.g. Sörnmo, "A Model-based Approach to QRS Delineation", Computers and Biomedical Research, Vol. 20, pp. 526–542 (1987). After the correlation coefficient has been calculated for each lead and each reference, threshold values are applied to determine the class to which the QRS complex is to be assigned.

Figure 6A:
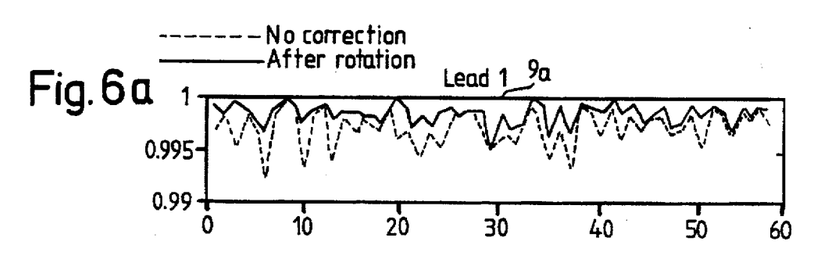
FIGS. 6a–6c show the cross-correlation between the reference heartbeat and all the other heartbeats before and after rotation and scaling according to the invention.
Figure 6B:
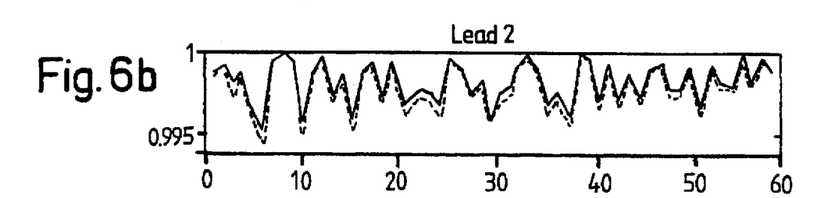
Figure 6C:
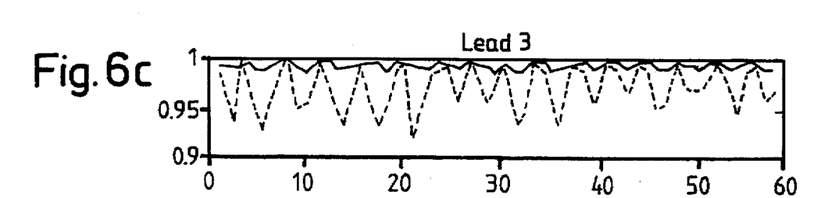

The present invention offers an advantageous alternative to traditional morphology classification. The Frobenius norm for the difference matrix between the reference matrix and the optimally synchronized, scaled and rotated matrix, representing the currently measured QRS complex, is thus calculated as a measure of likeness. This technique has the advantage that values from several leads need not be combined. One single comparison between the Frobenius norm and a threshold value is sufficient. FIGS. 3a and 3b, 4a and 4b, and 5a and 5b show the three orthogonal leads for QRS complexes from 50–60 heartbeats, before and after optimum correction, according to the invention, by rotation in relation to a "correct" reference complex, and FIGS. 6a–6c show the changes in corresponding correlation coefficient before and after the correction. FIGS. 6a–6c show that the correlation coefficient for lead 3, for which correlation was worst, improved considerably by correction according to the invention, whereas the other two leads, for which the correlation was high already from the beginning, were only affected marginally. It should be noted that the scale on the vertical axis differs for the three leads shown.

These figures clearly illustrate that morphology classification can be performed with much greater certainty after correction by rotation and scaling according to the invention.

Figure 7A:
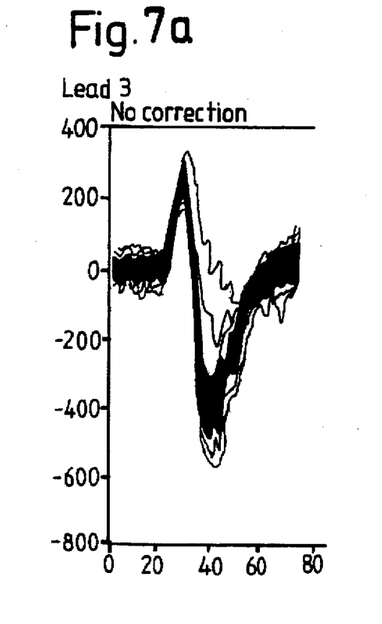
FIGS. 7a and 7b show shows one of three leads in another ECG recording of a larger number of cycles, time-synchronized and superimposed on each other.
Figure 7B:
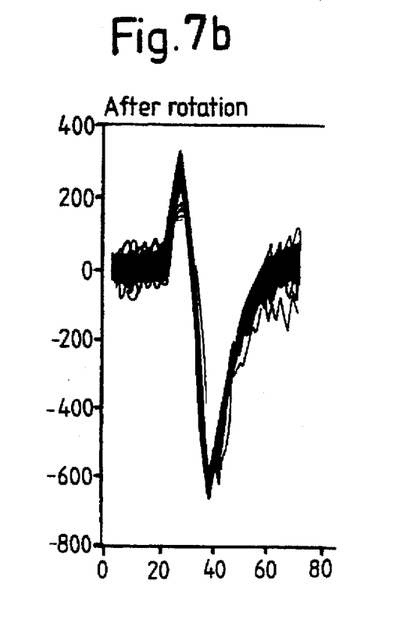
Figure 8A:
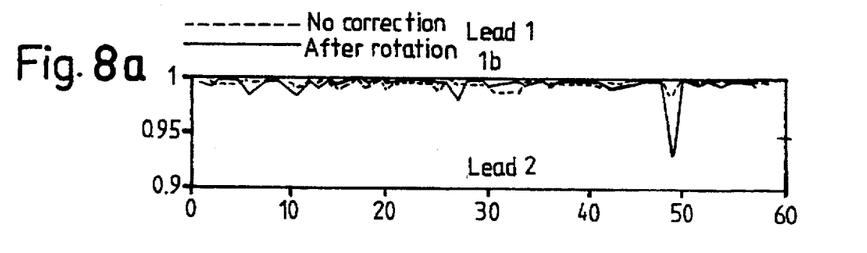
FIGS. 8a–8c show the cross-correlation between the reference beat in this instance and the other beats before and after rotation and scaling according to the invention.
Figure 8B:
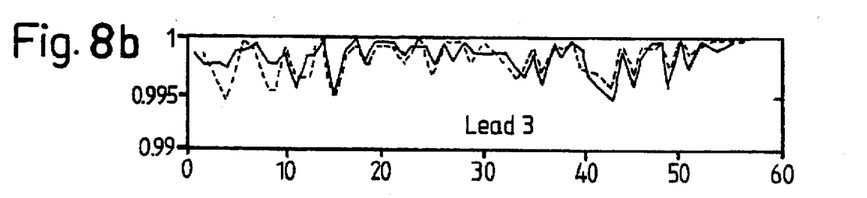
Figure 8C:
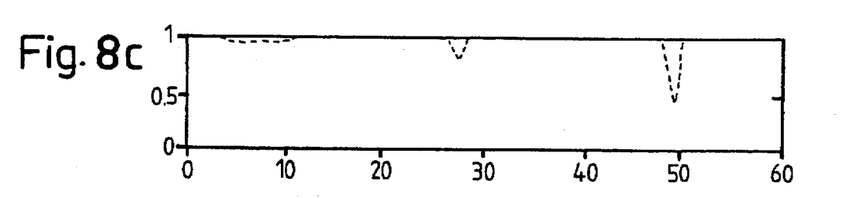

FIGS. 7a–7c show diagrams corresponding to those of FIGS. 3a–5b for one lead for QRS complexes from 58 consecutive beats, wherein two heartbeats risk erroneous classification due to very poor correlation in the lead shown. Erroneous classification is no longer a risk after correction according to the invention of the direction of the electrical axis. The correlation is then high for all leads, as shown in FIGS. 8a–8c. It should be noted that the vertical axis also in this figure have different scales for the three leads.

One exemplary embodiment has been described above for morphology classification of QRS complexes, however, the invention is suitable for several other applications. Instead of the QRS complex, other characteristic parts of a heart beat, such as the P wave, can be studied, as noted above and the invention is useful for analysis of variance ECG and for so-called serial comparison of resting ECGs in order to compensate for variations in electrode placement. The invention can also be used for monitoring of patients for longer periods of time during which the patient e.g., turns over from time to time, causing a change in the position of the electrodes in relation to the heart.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for correcting for non-physiological variations in ECG signals, comprising the steps of:

(a) recording ECG signals from a patient using a plurality p of electrodes over successive heartbeats to obtain an ECG signal for each heartbeat of said successive heartbeats;

(b) conditioning and digitizing at least a portion of each of said ECG signals to obtain m signal samples;

(c) storing said signal samples in an m×p measuring matrix;

(d) providing a predetermined reference matrix; and (e) minimizing a difference between said measuring matrix and said predetermined reference matrix by performing at least one matrix operation on said measuring matrix selected from the group of matrix operations consisting of translation, time synchronization, rotation and scaling, to obtain a corrected matrix.

2. A method as claimed in claim 1 wherein the step of minimizing the difference between said measuring matrix and said reference matrix includes subtracting one of said reference matrix or said measuring matrix from the other to obtain a difference matrix, and determining a Frobenius norm of said difference matrix as a measure of the difference between said measuring matrix and said reference matrix.

3. A method as claimed in claim 1 wherein said measuring matrix comprises a first measuring matrix comprising the additional step of obtaining a plurality of time-successive measuring matrices from said ECG signals after said first measuring matrix by successively repeating steps (a), (b) and (c), and selecting time synchronization as said matrix operation, and performing said time synchronization by shifting samples in a measuring matrix by one sample for each successive measuring matrix, and selecting a measuring matrix exhibiting a smallest difference compared to said reference matrix as a time-synchronized measuring matrix.

4. A method as claimed in claim 1 comprising selecting rotation and scaling as matrix operations to perform on said measuring matrix, and performing matrix rotation and matrix scaling simultaneously on said measuring matrix.

5. A method as claimed in claim 1 wherein the step of providing a reference matrix comprises obtaining a plurality of corrected measuring matrices using said method by temporarily using one of said measuring matrices as said reference matrix, obtaining an average value matrix which is an average of said corrected matrices, and thereafter using said average value matrix as said reference matrix.

6. A method as claimed in claim 5 wherein the step of providing a reference matrix further comprises including each successively obtained measuring matrix in the formation of said average value matrix currently used as said reference matrix until a change in said average value falls below a predetermined value.

7. A method as claimed in claim 5 comprising the additional step of subtracting one of a current corrected matrix, obtained from a current measuring matrix, and a current average value matrix used as the reference matrix from each other to obtain a difference matrix and determining a Frobenius norm of the difference matrix, and excluding any measuring matrix from use in forming said average value matrix which produces a Frobenius norm deviating by a predetermined amount from a predetermined value of the Frobenius norm.

8. A method as claimed in claim 1 wherein the step of selecting at least one matrix operation from said group comprises the steps of selecting time synchronization as a matrix operation performed first on said measuring matrix, determining a difference between a current measuring matrix and said reference matrix, and selecting rotation and scaling as further matrix operations and performing rotation and scaling on said current measuring matrix if said difference is less than a predetermined value.

9. A method as claimed in claim 1 comprising the additional step of providing a predetermined morphology classification, wherein step (b) includes selecting a portion of said ECG signal in each heartbeat corresponding to a ORS complex for producing said signal samples, and, after obtaining said corrected matrix, classifying the QRS complex represented by the corrected matrix according to said predetermined morphology classification.

10. A method as claimed in claim 9 wherein the step of classifying the corrected matrix comprises storing a plurality of class reference matrices respectively representing different morphology classes, forming a difference matrix between said corrected matrix and each class reference matrix, calculating a Frobenius norm for each difference matrix, and assigning said corrected matrix to a morphology class dependent on said Frobenius norm.

11. A method as claimed in claim 9 wherein step (a) includes obtaining a waveform from each of said electrodes, and wherein the step of classifying said corrected matrix comprises calculating a correlation coefficient with respect to a reference value for each waveform from the respective electrodes, and comparing each correlation coefficient to a predetermined threshold value.

12. A method as claimed in claim 1 wherein the step of providing a reference matrix comprises generating said reference matrix from at least a portion of an immediately preceding heartbeat, relative to a current measuring matrix, of said patient.

13. An apparatus for correcting for non-physiological variations in ECG signals, comprising:

recording means for recording ECG signals from a patient using a plurality p of electrodes over successive heartbeats for obtaining an ECG signal for each heartbeat of said successive heartbeats;

signal conditioning means for conditioning and digitizing at least a portion each of said ECG signals to obtain m signal samples;

first storage means for storing said signal samples in an m×p measuring matrix; second storage means for storing a predetermined reference matrix; and calculation means for minimizing a difference between said measuring matrix and said reference matrix by performing at least one matrix operation on said measuring matrix selected from the group of matrix operations consisting of translation, time synchronization, rotation and scaling, to obtain a corrected matrix.

14. An apparatus as claimed in claim 13 wherein said calculating means includes means for subtracting one of said reference matrix or said measuring matrix from the other to obtain a difference matrix, and for determining a Frobenius norm of said difference matrix as a measure of the difference between said measuring matrix and said reference matrix.

15. An apparatus as claimed in claim 13 wherein said signal conditioning means comprise high pass filter means for filtering out baseline variations in said ECG signals.

16. An apparatus as claimed in claim 13 wherein said calculation means comprise QRS detector means for identifying QRS complexes in said signal samples and for minimizing a difference between a QRS complex in said measuring matrix and a QRS complex in said reference matrix by performing said at least one matrix operation.

17. An apparatus as claimed in claim 16 wherein said first storage means comprise means for storing a plurality of time-successive measuring matrices respectively containing signal samples of QRS complexes from said successive heartbeats and wherein said calculation means comprise means for performing time synchronization as said matrix operation, and said calculation means including means for performing said time synchronization by shifting samples in said measuring matrix by one sample for each successive measuring matrix, and selecting a measuring matrix exhibiting a smallest difference compared to said reference matrix as a time-synchronized measuring matrix.

18. An apparatus as claimed in claim 17, wherein said QRS complex has an electrical axis and wherein said calculation means comprise means for calculating a Frobenius norm for a difference matrix between a measuring matrix containing a current QRS complex, and said reference matrix for different rotation positions of the electrical axis of the QRS complex, and for continuing said rotation until the Frobenius norm is as small as possible.

19. An apparatus as claimed in claim 18 wherein said calculation means comprise means for scaling the measuring matrix, containing the current QRS complex which gives the smallest value of the Frobenius norm.

20. An apparatus as claimed in claim 16 comprising means for classifying the QRS complex represented by the corrected matrix according to a predetermined morphology classification.

21. An apparatus as claimed in claim 20 wherein the means for classifying the corrected matrix comprise means for storing a plurality of class reference matrices respectively representing different morphology classes, means for forming a difference matrix between said corrected matrix and each class reference matrix, means for calculating a Frobenius norm for each difference matrix, and means for assigning said corrected matrix to a morphology class dependent on said Frobenius norm.

22. An apparatus as claimed in claim 20 wherein said means for classifying said corrected matrix comprises means for calculating a correlation coefficient with respect to a reference value for each waveform from the respective electrodes, and means for comparing each correlation coefficient to a predetermined threshold value.

23. An apparatus as claimed in claim 22 wherein said calculation means comprise means for generating a new reference matrix containing a new reference QRS complex for use by said means for classifying if said correlation coefficient is less than said predetermined threshold value.

\* \* \* \* \*